(12) United States Patent
Barger

(10) Patent No.: US 6,440,678 B1
(45) Date of Patent: Aug. 27, 2002

(54) MATERIALS AND METHODS RELATED TO THE INFLAMMATORY EFFECTS OF SECRETED AMYLOID PRECURSOR PROTEINS

(75) Inventor: Steven W. Barger, Conway, AR (US)

(73) Assignee: Board of Trustees of University of Arkansas, Little Rock, AR (US)

(*) Notice: Subject to any disclaimer, the term of this patent is extended or adjusted under 35 U.S.C. 154(b) by 0 days.

(21) Appl. No.: 09/141,951

(22) Filed: Aug. 28, 1998

(51) Int. Cl.$^7$ .............................. G01N 33/53
(52) U.S. Cl. .................. 435/7.1; 435/305; 435/366; 435/368
(58) Field of Search ................ 435/7.1, 325, 366, 435/368

(56) References Cited

PUBLICATIONS

Barger, S. W., *Society for Neuroscience Abstracts*, 22(3):2139, 1996.*
Mattson et al., 10 *Neuron* 243 (1993).
Smith–Swintosky, et al., 63 *J Neurochem* 781 (1994).
Barger & Mattson, 69(1) *J Neurochem* 60 (1997).
Furukawa et al., 67 *J Neurochem* 1882 (1996).
Barger & Mattson, 40 *Mol Brain Res* 116(1996).
Oltersdorf et al., 341 *Nature* 144 (1989).
Barger & Harmon, 388 *Nature* 878 (1997).

* cited by examiner

*Primary Examiner*—Marianne P. Allen
(74) *Attorney, Agent, or Firm*—Kilpatrick & Stockton LLP

(57) ABSTRACT

The present invention provides, inter alia, methods and materials useful to affect the inflammatory/and or neuroprotective effects of secreted amyloid precursor protein. In one broad aspect of the present invention, there are provided methods to reduce inflammation caused by sAPP in the brain of a mammal in need of such reduction, comprising administering a pharmaceutically-effective amount of a compound which inhibits the amino terminal region of sAPP involved in inflammatory response. In particular, a method as described, wherein the amino terminal region inhibited comprises $Val^{20}$ to $Tyr^{303}$ (using the $\beta APP_{695}$ numbering system) is provided, although a method as above, wherein the amino terminal region inhibited comprises the region which binds ApoE is also provided.

3 Claims, 1 Drawing Sheet

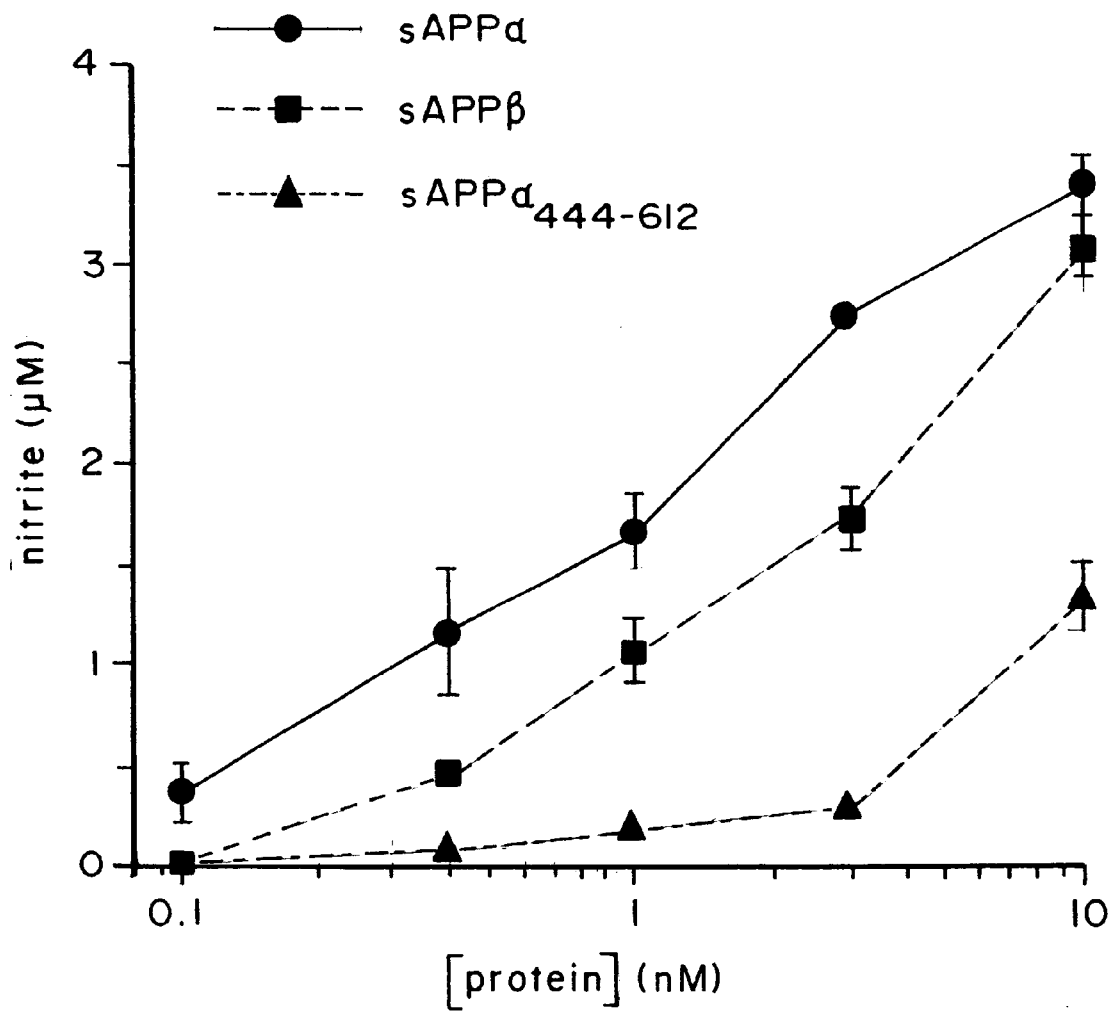
FIG. I

MATERIALS AND METHODS RELATED TO THE INFLAMMATORY EFFECTS OF SECRETED AMYLOID PRECURSOR PROTEINS

BACKGROUND OF THE INVENTION

Unchecked inflammation in the brain results in neural tissue necrosis which can manifest as seizures, dementia, loss of mental capacities, or death. For example, epilepsy, dementia due to Alzheimer's disease, stroke and traumatic brain injury have all been linked to dysfunctional inflammatory responses, although causal relationships between agents responsible for inducing the inflammatory response and the inflammatory response thereby induced have been speculative.

With regard to Alzheimer's disease, one agent, the secreted amyloid precursor protein (sAPP) has been shown to be neuroprotective, (Mattson et al., 10 *Neuron* 243 (1993) and Smith-Swintosky et al., 63 *J Neurochem* 781 (1994) and the regulator ApoE has been shown to potentiate the neuroprotective activity of sAPPα. Barger and Mattson, 69(1) *J Neurochem* 60 (1997). The extent of neuroprotection was shown in Barger and Mattson to vary among allelic variants of apolipoprotein E (ApoE), with ApoE3 apparently being superior to ApoE4 in its ability to induce the neuroprotective effects. ibid. It was speculated in Barger and Mattson that individuals who carried at least one ApoE4 allele had reduced sAPP-related neuroprotection, due to ineffectual inhibition of phosphoinositides, and resulting detrimental calcium ion increases. Furukawa et al., 67 *J Neurochem* 1882 (1996), showed the neuroprotection to result from residues 596–612, the existence of these residues in sAPPα distinguish sAPPα from sAPPβ.

Alzheimer's disease currently affects 4 million Americans. The cumulative health care costs associated with Alzheimer's, stroke and traumatic brain injury are $155 billion/year in the United States. Americans desperately need treatments which ameliorate the symptoms of these diseases and injuries.

Citation of the above documents is not intended as an admission that any of the foregoing is pertinent prior art. All statements as to the date or representation as to the contents of these documents is based on subjective characterization of information available to the applicant, and does not constitute any admission as to the accuracy of the dates or contents of these documents.

SUMMARY OF THE INVENTION

It is therefore an object of the present invention to provide materials useful in assays for agents to treat inflammation related to sAPP.

It is a further object to provide methods to reduce the negative inflammatory effects of sAPP.

It is yet another object to provide methods to potentiate the positive neuroprotective effects of sAPPα by inhibiting the inflammatory effects of that molecule.

It is yet another object to provide research materials and methods useful to study sAPP.

BRIEF DESCRIPTION OF THE DRAWINGS

FIG. 1 Structural requirements for sAPP stimulation of microglia. Constructs containing the coding sequences of human sAPPα, sAPPβ, and sAPPα$^{444-612}$ were expressed in *E. coli* and purified to apparent homogeneity. Primary microglia were treated with 0.1–10 nM of each protein. After 24 hours, the culture medium was tested for the presence of nitrite with Griess reagents. Values represent the mean ±SEM for triplicate determinations within a single experiment that was representative of three performed. Results for sAPPα$^{444-612}$ were significantly different from those for sAPPα and sAPPβ (p<0.0003 and p<0.04, respectively); the difference between sAPPα and sAPPβ was not significant.

DETAILED DESCRIPTION OF THE INVENTION

The present invention provides, inter alia, methods and materials useful to affect the inflammatory/and or neuroprotective effects of secreted amyloid precursor protein. In one broad aspect of the present invention, there are provided methods to reduce inflammation caused by sAPP in the brain of a mammal in need of such reduction, comprising administering a pharmaceutically-effective amount of a compound which inhibits the amino terminal region of sAPP involved in inflammatory response. In particular, a method as described, wherein the amino terminal region inhibited comprises Val$^{20}$ to Tyr$^{303}$ (using the βAPP$_{695}$ numbering system) is provided, although a method as above, wherein the amino terminal region inhibited comprises the region which binds ApoE is also provided.

Any mammal which is prone to, or experiencing, the negative inflammation-producing effects of sAPP is subject to the present invention. Humans are the preferred subjects. In particular, humans with reduced levels of ApoE3, whether experiencing symptoms or not, are subject to the present methods. Whether a person carries the ApoE3 allele can be determined according to many assays, for example, according to ie. U.S. Pat. Nos.: 5,767,248; 5,756,067; 5,747,260; 5,716,828; 5,508,167; and 4,772,549 or other known methods. Moreover, those individuals which have diseases due to the pro-inflammation effects of sAPP, whether the disease is acute or not, are subject to the present invention. Persons with epilepsy, stroke, traumatic brain injury and Alzheimer's disease are particularly likely to benefit from the present invention.

The pharmaceutical compound or compounds used in the present method can be any known compound or any compound discovered in the future, so long as the compound can reduce the inflammatory effects of sAPP. ApoE3 is a preferred such compound, although anti-sense nucleic acid which will inhibit production of at least the amino terminus of sAPP is also within the scope of the present invention.

ApoE3 can be obtained from recombinant expression systems or purification of human plasma and administered according to Aebischer et al., 2(6) *Nat Med* 696 (1996). In addition, compromise of the blood-brain barrier during disease (e.g. Skoog et al., 50(4) *Neurol* 966 (1998) may permit administration of ApoE3 intravascularly. Antisense constructs can be prepared according to Sambrook et al., *Molecular Cloning. A Laboratory Manual* (Cold Spring Harbor Laboratory Press, 1989) and Ausubel et al., *Current Protocols in Molecular Biology* (Greene Publishing Associates, Inc., 1993).

In another broad aspect of the present invention, there are provided methods to potentiate the neuroprotective effects of sAPPα in a person in need of such potentiation, comprising administering a pharmaceutically-effective amount of compound which inhibits the amino-terminal region of sAPPα involved in inflammatory response. A method as above, wherein the amino terminal region inhibited comprises Val$^{20}$ to Tyr$^{303}$ using the βAPP$_{695}$ numbering system is a preferred embodiment of the methods of this aspect of the invention, although a method wherein the amino terminal region inhibited comprises the region which binds ApoE is also included.

As described for the inflammation-reducing aspect of the present invention, any mammal which is prone to, or experiencing, the negative inflammation-producing effects of sAPPα is subject to the present invention. Humans are the preferred subjects. In particular, humans with reduced levels of ApoE3, whether experiencing symptoms or not, are subject to the present methods. Whether a person carries the ApoE3 allele can be determined according to many assays, for example, according to previously mentioned procedures. Moreover, those individuals which have diseases due to the pro-inflammation effects of sAPPα, whether the disease is acute or not, are subject to the present invention. Persons with epilepsy, stroke, traumatic brain injury and Alzheimer's disease are particularly likely to benefit from the present invention.

Moreover, the pharmaceutical compound or compounds used in the present methods can be any known compound or any compound discovered in the future, so long as the compound can potentiate the neuroprotective effects of sAPPα. ApoE3 is a preferred such compound, although anti-sense nucleic acid which will bind at least the amino terminus of sAPPα is also within the scope of the present invention. These compounds can be obtained and administered as described above for the methods to affect inflammation.

With regard to the materials provided in the present invention, there are amino acid compounds and nucleic acid compounds disclosed. The compounds are all useful in assays for compounds which affect inflammatory effects of sAPP. These materials are also useful in scientific research pertaining to sAPPs. In particular, an amino acids consisting essentially of SEQ ID NO 1 are provided. Also provided are methods to recombinantly produce an amino acid of SEQ ID NO 1, comprising expressing SEQ ID NO 2. SEQ ID NO 2 has this sequence:

be expected to be found within a given individual since the genome is diploid and/or among a group of two or more individuals. The present invention also includes variants due to laboratory manipulation, such as, but not limited to, variants produced during polymerase chain reaction amplification or site directed mutagenesis. It is also well known that there is a substantial amount of redundancy in the various codons which code for specific amino acids. Therefore, this invention is also directed to those nucleic acid sequences which contain alternative codons which code for the eventual translation of the identical amino acid. For example, substitution of valine for leucine, arginine for lysine, or asparagine for glutamine may not cause a change in functionality of the polypeptide.

Lastly, a nucleic acid sequence homologous to the exemplified nucleic acid compounds (or allelic variants or degenerates thereof) will have at least 90% sequence homology with the nucleic acid compounds in the sequence listing. Most preferred is a mRNA which is a transcript of a sequence listing nucleic acid. Stringent hybridization conditions are described in Sambrook et al., *Molecular Cloning. A Laboratory Manual* (Cold Spring Harbor Laboratory Press, 1989)

A variety of procedures known in the art may be used to molecularly clone the present nucleic acids. These methods include, but are not limited to complementation for function following the construction of a genomic DNA library in an appropriate vector system. Another method is to screen a genomic DNA library constructed in a bacteriophage or plasmid shuttle vector with a labeled oligonucleotide probe designed from the amino acid sequence of the gene. An additional method consists of screening genomic DNA libraries constructed in a bacteriophage or plasmid shuttle vector with a partial DNA encoding the gene. This partial DNA is obtained by specific PCR amplification of the gene DNA fragments through the design of degenerate oligonucleotide primers from the amino acid sequence of the purified gene product or by using another member of the gene family as a probe. Sambrook et al., *Molecular Cloning.*

```
5'-GTACCCACTGATGGTAATGCTGGCCTGCTGGCTGAACCCCAGATTGCCATGTTCTGTGGCAGAC

TGAACATGCACATGAATGTCCAGAATGGGAAGTGGGATTCAGATCCATCAGGGACCAAAACCTGCATTCATA

CCAAGGAAGGCATCCTCCAGTATTGCCAAGAAGTCTACCCTGAACTGCAGATCACCAATGTGGTAGAAGCCA

ACCAACCAGTGACCATCCAGAACTGGTCCAAGCGGGGCCGCAAGCAGTGCAAGACCCATCCCCACTTTGTGA

TTCCCTACCGCTGCTTAGTTGGTGAGTTTGTAAGTGATGCCCTTCTCGTTCCTGACAAGTGCAAATTCTTAC

ACCAGGAGAGGATGGATGTTTGCGAAACTCATCTTCACTGGCACACCGTCGCCAAAGAGACATGCAGTGAGA

AGAGTACCAACTTGCATGACTACGGCATGTTGCTGCCCTGCGGAATTGACAAGTTCCGAGGGGTAGAGTTTG

TGTGTTGCCCACTGGCTGAAGAAAGTGACAATGTGGATTCTGCTGATGCGGAGGAGGATGACTCGGATGTCT

GGTGGGGCGGAGCAGACACAGACTATGCAGATGGGAGTGAAGACAAAGTAGTAGAAGTAGCAGAGGAGGAAG

AAGTGGCTGAGGTGGAAGAAGAAGAAGCCGATGATGACGAGGACGATGAGGATGGTGATGAGGTAGAGGAAG

AGGCTGAGGAACCCTACGAAGAAGCCACAGAGAGAACCACCAGCATTGCCACCACCACCACCACCACCACAG

AGTCTGTGGAAGAGGTGGTTCGAGTTCCTACAACAGCAGCCAGTACCCCTGATGCCGTTGACAAGTAT-3'
```

Nucleic acids consisting essentially of SEQ ID NO 2 are provided, as are vectors and cells comprising that sequence.

Included within the scope of the present invention, with particular regard to the nucleic acids above, are allelic variants, degenerate sequences and homologues. Allelic variants are well known to those skilled in the art and would

*A Laboratory Manual* (Cold Spring Harbor Laboratory Press, 1989) and Ausubel et al., *Current Protocols in Molecular Biology* (Greene Publishing Associates, Inc., 1993) describe these procedures. Alternatively, the nucleic acids can be prepared as exemplified herein. When the nucleic acid is prepared or altered synthetically, advantage can be taken of known codon preferences of the intended host where the nucleic acid is to be expressed.

The cloned nucleic acids may be expressed through methods known in the art. The DNA can be recombinantly expressed by molecular cloning into an expression vector containing a suitable promoter and other appropriate transcription regulatory elements, and transferred into prokaryotic or eukaryotic host cells to produce recombinant gene product. Techniques for such manipulations are fully described in Sambrook et al., *Molecular Cloning. A Laboratory Manual* (Cold Spring Harbor Laboratory Press, 1989). Expression vectors can be used to express genes in a variety of hosts such as bacteria, bluegreen algae, plant cells, insect cells, fungal cells and animal cells. Expression vectors may include, but are not limited to, cloning vectors, modified cloning vectors, specifically designed plasmids or viruses.

Amino acid compounds which would result from manipulation and expression of the nucleic acid compounds herein disclosed are preferred embodiments of the present invention, with the amino acid compounds which would result from expression of the exemplified compounds being most preferred. Certain modifications, such as adding start codons or promoters or enhancers may be necessary to express the present amino acid compounds via the DNA compounds herein provided, and such manipulations are well known in the art. It is understood that amino acid compounds which would result from expression of allelic variants of the exemplified sequences, as well as amino acid compounds which would result from the expression of nucleic acid compounds which hybridize under stringent hybridization conditions to the nucleic acid compounds exemplified are within the scope of the present invention as well. Lastly, an amino acid sequence substantially homologous to a referent protein will have at least 90% sequence homology with the amino acid sequence of a referent protein or a peptide thereof. Also included within the scope of this invention are mutations either in the nucleic acid sequence or the translated protein which do not substantially alter the ultimate physical properties of the expressed protein. SEQ ID NO 1 is the most preferred amino acid compound, and has this sequence:

test compound binds. A method as described wherein the region comprises SEQ ID NO 1 is preferred, with a method wherein binding is determined via bioassay of inflammatory effects also being preferred. Coprecipitation assays can also be used. Coprecipitation assays can be performed according to Barger & Mattson, 69 *J Neurochem* 60 (1997).

EXAMPLES

The following cells, reagents and methods were used in these examples:

Cells and Reagents

Primary microglia were subcultured to approximately 95% purity from neonatal rat mixed glial cultures by differential adherence and panning techniques. Unless otherwise indicated, they were subcultured in minimal essential medium (MEM) supplemented to 10% with fetal bovine serum (FBS). The N9 cell line is a myc-immortalized murine microglial cell line generated by Dr. Paola Ricciardi-Castagnoli (U. Milan, Italy); they were maintained in MEM/10% FBS and switched to serum-free MEM 18–24 h before stimulation. Primary cultures of hippocampal neurons were established from E18 rats as described previously in Barger & Mattson, 40 *Mol Brain Res* 116 (1996). Unless otherwise indicated, sAPP was purified (>98% homogeneity) from the conditioned medium of HEK$^{293}$ transfectants as described previously Barger & Mattson, 40 *Mol. Brain Res* 116 (1996). The protein produced in this system is generated from βAPP$^{695}$ and has a carboxyterminus consistent with α-secretase processing Oltersdorf et al., 341 *Nature* 144 (1989). Bacterially expressed protein for structural comparisons was generated from sequence coding for Val$^{20}$-Lys$^{612}$ of human βAPP$^{695}$ ("sAPPα") placed in a pTrcHis (InVitrogen) expression vector. This vector tags expressed proteins aminoterminally with a polyhistidine sequence to allow one-step purification on a nickel-affinity column. A second construct ("sAPPβ") was generated with a stop codon after Met$^{596}$. The third construct ("sAPPα$^{444\text{-}612}$") was made from sAPPα by deletion of coding sequences aminoterminal to Asp$^{444}$. To exclude the possibility of contamination by bacterial endotoxin, some assays of these bacterially expressed proteins were performed in the presence of 10 μg/ml polymyxin-β sulfate. Human recombinant

```
VPTDGNAGLLAEPQIAMFCGRLNMHMNVQNGKWDSDPSGTKTCIDTKEGILQYCQEVYPEL

QITNVVEANQPVTIQNWCKRGRKQCKTHPHFVIPYRCLVGEFVSDALLVPDKCKFLHQERM

DVCETHLHWHTVAKETCSEKSTNLHDYGMLLPCGIDKFRGVEFVCCPLAEESDNVDSADAE

EDDSDVWWGGADTDYADGSEDKVVEVAEEEEVAEVEEEEADDDEDDEDGDEVEEEAEEPYE

EATERTTSTATTTTTTTESVEEVVRVPTTAASTPDAVDKY
```

Also provided in the present invention are the assays alluded to above. In particular, there are provided methods to identify the ability of a test compound to inhibit the inflammatory affects of sAPP, comprising contacting the test compound with sAPP in the presence of cells which are known to produce at least one marker of inflammation, and determining whether at least one marker of inflammation is induced. A method as described, wherein the marker is nitrite production is preferred.

Also provided are methods to identify the ability of a test compound to bind to the region of sAPP responsible for negative inflammatory effects, comprising contacting the test compound with the region of sAPP responsible for negative inflammatory effects, and determining whether the ApoEs were obtained from Pan Vera (Madison Wis.), and were not delipidated or subjected to reducing agents during purification. Antibodies included anti-iNOS monoclonal (Transduction Laboratories), hamster a-murine IL-1β monoclonal (Genzyme), and anti-ApoE monoclonal (Chemicon). Coincubations of sAPP and ApoE were performed at room temperature for 45 min (polyhistidine-tagged sAPP) or 60 min (HEK$^{293}$-expressed sAPP). For physiological assay the proteins were coincubated at 30 nM each; for biochemical assay (precipitation) the coincubation concentrations were 300 nM (polyhistidine-tagged sAPP) or 450 nM (HEK$^{293}$-expressed sAPP). Precipitation reactions were performed essentially as described Barger & Mattson, 69 *J. Neurochem.* 60 (1997).

EMSA

Nuclear extracts were prepared by the method of Ostrowski et al., 266 *J Biol Chem*12722 (1991). Five µg of extracted protein from each treatment condition was incubated with a $^{32}$P-labeled, κB DNA probe in EMSA buffer (50 mM Tris-HCl [pH 7.4], 20% glycerol, 50 mM NaCl, 5 mM MgCl2, 2.5 mM EDTA, 0.5% Nonidet P-40, 5 mM β-mercaptoethanol, and 250 µg/ml poly dI-dC). Electrophoresis was performed as described Barger & Mattson, 40 *Mol Brain Res* 116 (1996).

Nitrite Assay

For determination of nitrite, 100 µl of culture medium was removed and mixed with an equal volume of 0.5% sulfanilamide and 0.05% naphthylethyleneamine dihydrochloride in 0.25% phosphoric acid. After 10 min, the resulting color reaction was measured in a spectrophotometer at 540 nm, and the readings were calibrated to those obtained from standards containing known amounts of nitrite. Data are presented as the mean ±SEM for triplicate determinations within one of at least three similar experiments.

Statistics

Data were analyzed by ANOVA with Scheffe post-hoc, and p-values $\leq 0.05$ were assumed indicative of significance.

Example 1

Determination of the Impact of sAPP on the Inflammatory Reactions in Microglia

The N9 microglial cell line, described in Corradin et al., 7 *Glia* 255 (1993), was treated with sAPP and measured for NF-κB activity by electrophoretic mobility shift assay (EMSA). These cells responded to sAPP with an activation of NF-κB within 90 min. Induction of a κB-binding transcription factor by sAPP in primary neurons is dependent upon the elevation of cGMP8 and involves a transcription factor distinct from NF-κB (unpublished results). However, the addition of an inhibitor of cGMP-dependent protein kinase did not block the activation of NF-κB by sAPP in N9 cells, and a cell-permeant cGMP analog did not mimic the effects of sAPP in these cells. These results indicate that the activation of NF-κB by sAPP in microglial cells occurs through a cGMP-independent mechanism and thus could involve signaling events evoked by regions of sAPP distinct from the carboxyterminal sequences that stimulate cGMP-dependent neuromodulation.

Example 2

Determination Whether the Activation of NF-κB Translated into Elevated Gene Expression The levels of interleukin-1β (IL-1β) and inducible nitric oxide synthase (iNOS) in the N9 cell line and in primary cultures of microglia were examined. A 24-h treatment of primary microglia with 5 nM sAPP elevated immunocytochemical staining for IL-1β and iNOS. Elevated levels of IL-1β and iNOS also were apparent through western blot analysis of sAPP-treated microglia. The levels of IL-1β and iNOS in the N9 cell line responded to sAPP in a dose-dependent manner, with detectable induction occurring at 100 pM. Elevated expression of iNOS was apparent within 6 h of sAPP addition.

Example 3

Determination of the Role of the Carboxyterminal 16 Residues, with Regard to Two Secretase Products Recently, Furukawa et al. determined that the carboxyterminal 16 residues which distinguish the products of α- and β-secretase activity (sAPPα and sAPPβ, respectively) were critical for cGMP-dependent neuroprotective effects of sAPPα. Furukawa et al., 67 *J. Neurochem.* 1882 (1996). These findings were confirmed herein in a paradigm of neuronal death induced by 18-h glucose deprivation of primary hippocampal neurons, where treatment with 10 nM sAPPα resulted in a survival rate 222.3±19.6% of control (neurons subjected to glucose deprivation alone), and sAPPβ enhanced survival to only 126.5±12.0% of control. However, the Furukawa experiments were performed only in cultures lacking significant numbers of microglia. To explore the potential indirect effects of sAPP on neuronal survival mediated through microglia, the relationship between specific sAPP sequences and microglial activation were evaluated. As an index of activation, the culture medium of primary cultures of microglia was assayed for the presence of nitrite, a stable product of nitric oxide formation. Although there was a modest quantitative difference, both sAPPα and sAPPβ potently elevated nitrite levels in these cultures (FIG. 1). The neuroprotective activity of sAPPα is retained in a construct containing residues 444-612 (βAPP$^{695}$ numbering) Furukawa et al., 67 *J. Neurochem.* 1882 (1996); however, this construct was deficient in microglial activation (FIG. 1). These differences in structural requirements suggest that different domains of sAPP are involved in the protection of neurons and the activation of microglia, consistent with the lack of involvement of cGMP in the latter.

To test further the implications of this relationship, indirect neurotoxicity of sAPP in a paradigm where soluble factors can be applied to microglia, then removed before exposure of the microglia to primary neurons was tested. Primary microglia were plated on a permeable membrane suspended in the bottom of a culture-well basket. The cultures were pretreated for 24 h with 5 nM sAPPα, sAPPβ, or sAPPα$^{444-612}$, then washed and transferred to 35-mm wells containing primary hippocampal neurons. Viability of all neurons decreased by approximately 18% over the subsequent 48 h, and those exposed to untreated microglia were further compromised by an additional 34% (Table 1). However, toxicity was even greater in the presence of microglia that had been pretreated with sAPPα or sAPPβ; this correlation of microglial activation with neurotoxicity was extended to the deficient activity of sAPPα$^{444-612}$ in both assays.

TABLE 1

Indirect neurotoxicity of sAPPs.

| Basket contents | Neuronal survival (% of initial) | |
|---|---|---|
| | 24 h | 48 h |
| 1. None (neurons alone) | 93.1 ± 4.2 | 82.3 ± 6.7 |
| 2. Microglia, untreated | 67.2 ± 9.1 | 48.0 ± 7.6 |
| 3. Microglia pretreated with sAPPα | 37.4 ± 3.6* | 16.9 ± 5.7* |
| 4. Microglia pretreated with sAPPβ | 43.2 ± 5.0* | 24.6 ± 4.9* |
| 5. Microglia pretreated with sAPPα$^{444-612}$ | 70.2 ± 5.4 | 39.4 ± 0.3 |

All sAPP pretreatments were performed at a concentration of 3 nM. Neuronal survival was determined by a blinded observer using established morphological criteria from photographs of rat primary hippocampal neurons taken immediately before exposure to microglia ("initial") and at 24-h intervals thereafter. Data are expressed as the mean percentage (±SEM) of initial cell number present at each time point for triplicate cultures.

Example 4

Determination of Nitrite Production by ApoE4/sAPP v. ApoE3/sAPP Treated N9 Cells Recently, it was determined that bioactivities of sAPP can be modulated differentially by two forms of human apolipoprotein E (ApoE) which are encoded by gene alleles in disequilibrium with AD. Specifically, physical interaction of ApoE3 with sAPP inhibits an activity associated with the aminoterminal 443 residues; ApoE4 was less potent in this inhibition Barger & Mattson, 69 *J. Neurochem.* 60 (1997). Incubation with ApoE3 for 45 min also inhibited the ability of sAPPα to elevate nitrite production in N9 cells and to evoke microglia-mediated neurotoxicity; ApoE4 was less effective in both respects. Coprecipitation experiments revealed that ApoE3 was capable of binding sAPPα but not sAPPα444-612. The latter data support the hypothesis that ApoE3 binds and masks sAPP domains responsible for activating microglia. The relative deficiency of ApoE4 binding to sAPPα may explain its inability to affect sAPPα bioactivity.

Example 5

Determination of Region Responsible for Inflammatory Activity of sAPP

Previous studies have implicated an sAPPα region containing the sequence R-E-R-M-S (amino acids 328–332 in the βAPP$^{695}$ numbering system) in some biological activities of sAPPα. The deletion construct termed sAPP 444–612 (lacking the RERMS sequence) is deficient in pro-inflammatory activity (Barger and Harmon, 388 *Nature* 878 (1997). Therefore, additional experiments were performed to test the contribution of this RERMS region to pro-inflammatory activity of sAPPα. A deletion construct was generated that included Leu$^{304}$ through Lys$^{612}$. In assays of nitrite production in microglial cells, this construct also was inactive, demonstrating that the RERMS region is not sufficient to activate inflammatory events in microglia. The comparison to sAPPα indicates that amino acids Val$^{20}$-Tyr$^{303}$ are required for full pro-inflammatory activity.

TABLE 2

Structure/function analysis of RERMS region of sAPPα.

| Construct | Nitrite produced ($\mu$M) |
| --- | --- |
| None | 0.29 ± 0.03 |
| sAPPα, 10 nM | 4.22 ± 0.35* |
| sAPPα$^{444-612}$, 10 nM | 0.31 ± 0.01 |
| sAPPα$^{304-612}$, 10 nM | 0.32 ± 0.01 |
| sAPPα, 30 nM | 4.92 ± 0.23* |
| sAPPα$^{444-612}$, 30 nM | 0.79 ± 0.16 |
| sAPPα$^{304-612}$, 30 nM | 0.37 ± 0.03 |

*p < 0.001 vs. all other conditions (ANOVA and Scheffe post-hoc test)

Although the present invention has been fully described herein, it is to be noted that various changes and modifications are apparent to those skilled in the art. Such changes and modifications are to be understood as included within the scope of the present invention as defined by the appended claims.

What is claimed is:

1. A method to determine the ability of a test compound to inhibit the inflammatory effects of sAPP comprising the steps of:

(a) contacting the test compound with sAPP in the presence of N9 microglial cells in vitro; and (b) determining whether there is a change in nitrite production compared to a control where the test compound is absent, a reduction in nitrite production indicating that the test compound inhibits the inflammatory effects of sAPP.

2. The method of claim 1, wherein the test compound is ApoE.

3. The method of claim 2, wherein the test compound is ApoE3.

* * * * *

SEQUENCE LISTING

<160> NUMBER OF SEQ ID NOS: 2

<210> SEQ ID NO 1
<211> LENGTH: 284
<212> TYPE: PRT
<213> ORGANISM: Homo sapiens

<400> SEQUENCE: 1

```
Val Pro Thr Asp Gly Asn Ala Gly Leu Leu Ala Glu Pro Gln Ile Ala
 1               5                  10                  15

Met Phe Cys Gly Arg Leu Asn Met His Met Asn Val Gln Asn Gly Lys
                20                  25                  30

Trp Asp Ser Asp Pro Ser Gly Thr Lys Thr Cys Ile Asp Thr Lys Glu
            35                  40                  45

Gly Ile Leu Gln Tyr Cys Gln Glu Val Tyr Pro Glu Leu Gln Ile Thr
        50                  55                  60

Asn Val Val Glu Ala Asn Gln Pro Val Thr Ile Gln Asn Trp Cys Lys
 65                  70                  75                  80

Arg Gly Arg Lys Gln Cys Lys Thr His Pro His Phe Val Ile Pro Tyr
                85                  90                  95

Arg Cys Leu Val Gly Glu Phe Val Ser Asp Ala Leu Leu Val Pro Asp
            100                 105                 110

Lys Cys Lys Phe Leu His Gln Glu Arg Met Asp Val Cys Glu Thr His
        115                 120                 125

Leu His Trp His Thr Val Ala Lys Glu Thr Cys Ser Glu Lys Ser Thr
    130                 135                 140
```

```
Asn Leu His Asp Tyr Gly Met Leu Leu Pro Cys Gly Ile Asp Lys Phe
145                 150                 155                 160

Arg Gly Val Glu Phe Val Cys Cys Pro Leu Ala Glu Glu Ser Asp Asn
                165                 170                 175

Val Asp Ser Ala Asp Ala Glu Glu Asp Asp Ser Asp Val Trp Trp Gly
            180                 185                 190

Gly Ala Asp Thr Asp Tyr Ala Asp Gly Ser Glu Asp Lys Val Val Glu
            195                 200                 205

Val Ala Glu Glu Glu Val Ala Glu Val Glu Glu Glu Ala Asp
        210                 215                 220

Asp Asp Glu Asp Asp Glu Asp Gly Asp Glu Val Glu Glu Glu Ala Glu
225                 230                 235                 240

Glu Pro Tyr Glu Glu Ala Thr Glu Arg Thr Thr Ser Ile Ala Thr Thr
                245                 250                 255

Thr Thr Thr Thr Thr Glu Ser Val Glu Glu Val Val Arg Val Pro Thr
            260                 265                 270

Thr Ala Ala Ser Thr Pro Asp Ala Val Asp Lys Tyr
            275                 280

<210> SEQ ID NO 2
<211> LENGTH: 852
<212> TYPE: DNA
<213> ORGANISM: Homo sapiens

<400> SEQUENCE: 2
gtacccactg atggtaatgc tggcctgctg gctgaacccc agattgccat gttctgtggc      60
agactgaaca tgcacatgaa tgtccagaat gggaagtggg attcagatcc atcagggacc     120
aaaacctgca ttgataccaa ggaaggcatc ctgcagtatt gccagaagt ctaccctgaa      180 ctgcagatca ccaatgtggt agaagccaac caaccagtga ccatccagaa ctggtgcaag     240
cggggccgca agcagtgcaa gacccatccc cactttgtga ttccctaccg ctgcttagtt     300
ggtgagtttg taagtgatgc ccttctcgtt cctgacaagt gcaaattctt acaccaggag     360
aggatggatg tttgcgaaac tcatcttcac tggcacaccg tcgccaaaga gacatgcagt     420
gagaagagta ccaacttgca tgactacggc atgttgctgc cctgcggaat tgacaagttc     480 cgagggtag agtttgtgtg ttgcccactg gctgaagaaa gtgacaatgt ggattctgct     540
gatgcggagg aggatgactc ggatgtctgg tggggcggag cagacacaga ctatgcagat     600
gggagtgaag acaaagtagt agaagtagca gaggaggaag aagtggctga ggtggaagaa     660
gaagaagccg atgatgacga ggacgatgag gatggtgatg aggtagagga agaggctgag     720
gaaccctacg aagaagccac agagagaacc accagcattg ccaccaccac caccaccacc     780
acagagtctg tggaagaggt ggttcgagtt cctacaacag cagccagtac ccctgatgcc     840
gttgacaagt at                                                        852
```